(12) United States Patent
Burgaud et al.

(10) Patent No.: US 7,594,936 B2
(45) Date of Patent: Sep. 29, 2009

(54) DYE COMPOSITION FOR KERATIN FIBERS CONTAINING AN ALDEHYDE PRECURSOR, ENZYME AND HYDRAZONE, AND METHOD USING THIS COMPOSITION

(75) Inventors: Hervé Burgaud, Damartin en Goele (FR); Rui Pereira, Montevrain (FR); Béatrice Belcour-Castro, Joinville le Point (FR)

(73) Assignee: L'Oreal S.A., Paris (FR)

( * ) Notice: Subject to any disclaimer, the term of this patent is extended or adjusted under 35 U.S.C. 154(b) by 756 days.

(21) Appl. No.: 10/611,968

(22) Filed: Jul. 3, 2003

(65) Prior Publication Data

US 2004/0133992 A1 Jul. 15, 2004

Related U.S. Application Data

(60) Provisional application No. 60/408,897, filed on Sep. 9, 2002.

(30) Foreign Application Priority Data

Jul. 5, 2002 (FR) .................................. 02 08493

(51) Int. Cl.
*A61Q 5/10* (2006.01)
(52) U.S. Cl. .................. 8/405; 8/406; 8/409; 8/410; 8/412; 8/416; 8/423; 8/425
(58) Field of Classification Search ............... 8/405, 8/406, 408, 409, 410, 412, 416, 423, 425, 8/306
See application file for complete search history.

(56) References Cited

U.S. PATENT DOCUMENTS

| | | | | |
|---|---|---|---|---|
| 3,634,013 | A * | 1/1972 | Maul | 8/409 |
| 4,003,699 | A | 1/1977 | Rose et al. | 8/10.2 |
| 5,061,289 | A | 10/1991 | Clausen et al. | 8/405 |
| 5,380,340 | A | 1/1995 | Neunhoeffer et al. | 8/409 |
| 5,766,576 | A | 6/1998 | Löwe et al. | 424/62 |
| 6,099,592 | A | 8/2000 | Vidal et al. | 8/409 |
| 6,099,593 | A | 8/2000 | Terranova et al. | 8/409 |
| 2001/0044977 | A1 | 11/2001 | Mettrie et al. | 8/405 |
| 2002/0059682 | A1 * | 5/2002 | Hoeffkes et al. | 8/405 |

FOREIGN PATENT DOCUMENTS

| | | |
|---|---|---|
| DE | 23 34 738 | 1/1975 |
| DE | 23 59 399 | 6/1975 |
| DE | 38 43 892 | 6/1990 |
| DE | 41 33 957 | 4/1993 |
| DE | 195 43 988 | 5/1997 |
| DE | 199 49 033 | 4/2001 |
| EP | 0 310 675 | 4/1989 |
| EP | 0 770 375 | 5/1997 |
| FR | 2 733 749 | 11/1996 |
| FR | 2 750 048 | 12/1997 |
| FR | 2 769 219 | 4/1999 |
| FR | 2 822 062 | 9/2002 |
| GB | 1 026 978 | 4/1966 |
| GB | 1 153 196 | 5/1969 |
| JP | 2-19576 | 1/1990 |
| JP | 5-163124 | 6/1993 |
| WO | WO 94/08969 | 4/1994 |
| WO | WO 94/08970 | 4/1994 |
| WO | WO 96/15765 | 5/1996 |
| WO | WO 01/47478 | 7/2001 |
| WO | WO 01/68042 | 9/2001 |
| WO | WO 02/47633 | 6/2002 |

OTHER PUBLICATIONS

STIC Search Report dated Aug. 11, 2006.*
von Siegfried Hünig et al., "Azofarbstoffe Durch Oxydative Kupplung II Synthese Kupplungsfähiger Heterocyclischer 2-Hydrazone," Justus Liebigs Annalen Der Chemie, Verlag Chemie, Weinheim, DE, vol. 609, 1957, pp. 160-172.
English language Derwent Abstract of DE 23 34 738, Jan. 30, 1975.
English language Derwent Abstract of DE 199 49 033, Apr. 19, 2001.
English language Derwent Abstract of EP 0 770 375, May 2, 1997.
English language Derwent Abstract of FR 2 822 062, Sep. 20, 2002.
English language Derwent Abstract of JP 2-19576, Jan. 23, 1990.
English language Derwent Abstract of JP 5-163124, Jun. 29, 1993.

* cited by examiner

*Primary Examiner*—Eisa B Elhilo
(74) *Attorney, Agent, or Firm*—Finnegan, Henderson, Farabow, Garrett & Dunner LLP

(57) ABSTRACT

This application relates to a dye composition for dyeing keratin fibers, for example human keratin fibers, such as hair, comprising, in an appropriate dyeing medium, at least one aldehyde precursor, at least one enzyme able to generate an aldehyde from the at least one aldehyde precursor and at least one heteroaromatic hydrazone. This application also concerns a method for dyeing keratin fibers using the dye composition, and a dye "kit" containing the dye composition.

35 Claims, No Drawings

DYE COMPOSITION FOR KERATIN FIBERS CONTAINING AN ALDEHYDE PRECURSOR, ENZYME AND HYDRAZONE, AND METHOD USING THIS COMPOSITION

This application claims benefit of U.S. Provisional Application No. 60/408,897, filed Sep. 9, 2002.

Disclosed herein are compositions for dyeing keratin fibers. Also disclosed herein is a dye composition comprising at least one aldehyde precursor, at least one enzyme and at least one hydrazone, a method for dyeing keratin fibers using this dye composition, and a device with several compartments comprising this dye composition.

When dyeing keratin fibers, for example, human hair, it is known to use dye compositions comprising oxidation dye precursors, generally called oxidation bases, such as ortho or para-phenylenediamines, ortho or paraaminophenols and heterocyclic compounds. These oxidation bases can be colorless or scarcely colored compounds which, when associated with oxidizing products, may give rise to colored compounds via an oxidative condensation process.

It is also known that the shades obtained with oxidation bases can be varied by combining them with coloring couplers or modifiers. For example, modifiers chosen from among the aromatic metadiamines, metaaminophenols, metadiphenols and some heterocyclic compounds such as indole compounds can be used.

With the variety of molecules used as oxidation bases and couplers, a rich palette of colors can be obtained.

So-called "permanent" coloring obtained with oxidation dye compositions, must also meet a certain number of requirements. For example, oxidation dye compositions ideally should not have any disadvantages from a toxicological viewpoint. Also ideally, oxidation dye compositions should enable shades to be obtained with desired intensity and have good resistance against outside agents such as light, adverse weather conditions, washing, permanent waving, perspiration and friction.

Dye compositions should also, if possible, be able to cover grey hair and be the least selective possible, i.e., give the lowest possible color differences along one same keratin fiber, which is generally sensitised (damaged) to different extents between its tip and root.

Oxidation dyeing of keratin fibers is generally carried out in a highly alkaline medium in the presence of hydrogen peroxide. However, the use of alkaline media in the presence of hydrogen peroxide can have the drawback of leading to non-negligible deterioration of the keratin fibers, as well as decoloring of the keratin fibers, which is not always desirable.

Oxidation dyeing of keratin fibers may also be carried out using oxidizing systems other than hydrogen peroxide, such as enzyme systems. For example, patent application FR 2,769,219 (corresponding to U.S. Publication No. 2001/0044977 A1) describes the use of an uricase enzyme and its substrate uric acid in the oxidation dyeing of keratin fibers. As another example, patent application EP-A-0 310 675 describes the use of an oxidation dye precursor of benzene type in association with enzymes such as pyranose-oxidase and glucose-oxidase.

Aldehydes can also be used for dyeing keratin fibers. Patent application WO 01/62219 describes a dyeing composition for the dyeing of keratin fibers obtained by mixing two compounds: firstly a compound comprising at least one carbonyl bond such as an aldehyde, and secondly a compound of indole type or 3H indolium derivative.

The dye compositions disclosed herein are new compositions for dyeing keratin fibers, for instance, human keratin fibers, such as hair, wherein the dyeing compositions may be clean, non-toxic and respect the nature of keratin fibers.

The inventors have found, surprisingly and unexpectedly, dye compositions that are clean, non-toxic and respect the nature of keratin fibers, wherein such dye compositions comprise, in an appropriate dyeing medium, at least one aldehyde precursor, at least one enzyme able to generate an aldehyde from the aldehyde precursor, and at least one heteroaromatic hydrazone.

Thus, the dye compositions disclosed herein have the advantage of being able to be used in a dye medium of which water is the essential constituent. They may, therefore, be clean, non-toxic and respect the nature of keratin fibers.

These dye compositions can be used via a simple method that may avoid risks related to handling highly reactive products such as aldehydes. The aldehydes freshly produced by a biochemical route subsequently react with other molecules so that these aldehydes do not build up at the place where they are formed.

The dye compositions disclosed herein, can be used to obtain dyes of natural colors that are not very selective on keratin fibers and that provide resistant colors on the keratin fibers once dyed. These dye compositions can also generate new dyes that are capable of giving varied shades of intense, uniform color with no significant hair deterioration.

Also disclosed herein is a method for dyeing keratin fibers, for example, human keratin fibers such as hair, such method comprising applying the dye composition disclosed herein to keratin fibers for a sufficient time to develop the desired coloring.

The composition disclosed herein advantageously reacts in situ on keratin fibers by penetrating into and dyeing keratin fibers.

The at least one aldehyde precursor can be chosen from: amino acids chosen from N-6 methyl lysine, dimethylglycine, methyl glutamate, threonine and sarcosine; -2-oxo acids chosen from 2-oxoacidpyruvate, benzoylformate, and phenyl pyruvate; and primary alcohols chosen from methanol, ethanol, benzyl alcohol. For example, the aldehyde precursors can be primary alcohols chosen from primary aliphatic and aromatic alcohols, such as methanol, ethanol, propanol, and long chain hydrocarbon primary alcohols, such as $C_{12}$ to $C_{15}$ alcohols, benzyl alcohol, and 4-amino-benzyl alcohol.

The at least one enzyme that can generate an aldehyde from the at least one aldehyde precursor may be chosen from EC 1.1.1.1. alcohol dehydrogenases, EC 1.1.1.2 alcohol dehydrogenases, EC 1.1.1.71 alcohol dehydrogenases, EC 1.1.1.90 aromatic alcohol dehydrogenases (also called aryl alcohol dehydrogenases), EC 1.1.1.97 aromatic alcohol dehydrogenases, EC 1.1.1.97 3-hydroxybenzyl alcohol dehydrogenases, EC 1.1.1.194 coniferyl alcohol dehydrogenases, EC 1.1.1.195 cinnamyl alcohol dehydrogenases, EC 1.1.1.244 methanol dehydrogenases, EC 1.1.3.7 aromatic alcohol oxidases (also called aryl alcohol oxydases), EC 1.1.3.13 alcohol oxidases, EC 1.1.3.19 4-hydroxymandelate oxidases, EC 1.1.3.20 long chain hydrocarbon alcohol oxidases, EC 1.1.3.31 methanol oxidases, EC 1.1.99.20 alcohol dehydrogenases, EC 1.5.3.1 sarcosinase oxidases, EC 1.5.3.4 N6-methyl-lysine oxidases, EC 1.5.3.10 dimethylglycine oxidases, EC 1.5.99.1 sarcosine dehydrogenases, EC 1.5.99.2 dimethylglycine dehydrogenases, EC 1.5.99.5 methylglutamate dehydrogenases, EC 4.1.1.1 oxo-acid decarboxylases, EC 4.1.1.7 benzoyl-formate decarboxylases, EC 4.1.1 43 phenylpyruvate decarboxylases, and EC 4.1.2.5 threonine aldolases.

The at least one enzyme that can generate an aldehyde from the at least one aldehyde precursor used in the dye composition disclosed herein may be derived from an extract chosen from plant, animal, micro-organism extracts, viruses, differentiated cell, and dedifferentiated cell extracts, wherein the at least one enzyme may be obtained in vivo or in vitro, may or may not be genetically modified, and may be synthetic, i.e., obtained by chemical or biotechnological synthesis. For example, derivatives of the extracts of micro-organisms may originate from micro-organisms chosen from bacteria, fungi, yeast and microalgae.

Further examples of the at least one enzyme that can generate an aldehyde from the at least one aldehyde precursor may be derived from species chosen from *Plectranthus, Pinus, Gastropoda, Manduca, Pichia, Candida, Pleurotus*, and *Pseudomonas*. Even further examples of the at least one enzyme that can generate an aldehyde from the at least one aldehyde precursor may be derived from species of plant origin chosen from *Plectranthus colleoides*, and *Pinus strobes*; species of animal origin chosen from *Gastropoda mollusca*, and *Manduca sexta*; species of yeast origin chosen from *Pichia Pastoris* and *Candida boidinii*; fungi such as *Pleurotus pulmonarius*; and bacteria, such as *Pseudomonas pseudoalcaligenes*.

Generally, the concentration of the at least one enzyme used in the dye composition ranges from 0.005% to 40% by weight, relative to the total weight of the dye composition, for example, ranging from 0.05% to 10% by weight, relative to the weight of the dye composition.

The enzymatic activity of the at least one enzyme used in the dye composition may be defined using the oxidation of the donor (the at least one aldehyde precursor) under aerobic conditions. Unit U corresponds to the quantity of enzyme leading to generation of 1 μmole aldehyde per minute at a given pH and at a temperature of 25° C. For example, the quantity of enzyme ranges from 0.2 to $4.10^8$ U units per 100 g dye composition.

The choice of the at least one enzyme depends upon the type of at least one aldehyde precursor. For example, if the at least one aldehyde precursor is chosen from alcohols, then the at least one enzyme is chosen from enzymes able to generate an aldehyde from alcohols. For further example, if the at least one aldehyde precursor is methylglutamate, then the at least one enzyme is a methylglutamate dehydrogenase.

In one embodiment, the at least one aldehyde precursor is chosen from primary alcohols and thus the at least one enzyme chosen is able to generate an aldehyde from an alcohol. For example, if the at least one aldehyde precursor is a primary alcohol chosen from $C_1$ to $C_6$ aliphatic alcohols, then the at least one enzyme able to generate an aldehyde may be chosen from alcohol oxidases, alcohol dehydrogenases, methanol dehydrogenases, and methanol oxidases. If the at least one aldehyde precursor is a primary alcohol chosen from benzyl alcohol, 4-terbutyl benzyl alcohol, 3-hydroxy-4-methoxybenzyl alcohol, veratryl alcohol, 4-methoxy-benzyl alcohol, cinnamic alcohol, and 2,4 hexadiene-1-ol, then the at least one enzyme used to generate the aldehyde may be chosen from aryl alcohol oxidases and aromatic alcohol dehydrogenases.

Generally, the concentration of the at least one aldehyde precursor ranges from 0.01% to 40% by weight relative to the total weight of the composition. For example, the concentration of the at least one aldehyde precursor may range from 0.05% to 10% by weight, relative to the total weight of the composition.

The at least one hydrazone that may be used in the dye composition disclosed herein is a compound chosen from dye precursors able to generate a colored substance by reaction with an aldehyde, i.e., dye precursors. In one embodiment of the dye composition, the at least one hydrazone may be chosen from heteroaromatic hydrazones having the formula:

wherein Ar is an aromatic heterocycle with 5 or 6 links comprising at least one nitrogen atom. For example, in one embodiment, Ar is a heterocycle chosen from: pyrroles, pyridines, pyrazoles, and imidazoles. In another embodiment, Ar may be chosen from condensed polycyclic heteroaromatic groups with 9 or 10 links comprising at least one nitrogen atom, for example, an isoindole.

In yet another embodiment, Ar may be substituted on at least one position. For example Ar can be such that the nitrogen atoms of the heterocycle are substituted by a substituent chosen from $C_1$ to $C_4$ alkyls, (such as the methyl, ethyl, propyl and butyl groups), $C_1$ to $C_4$ alcohols (such as methanol (—$CH_2OH$), ethanol (—($C_2H_4$)OH), propanol (—$C_3H_6$) OH), and butanol (—($C_2H_8$)OH) groups), and $C_1$ to $C_4$ ethers (such as methoxy (—$OCH_3$), ethoxy (—$OC_2H_5$), propanoxy (—$OC_3H_7$), and butanoxy (—$OC_4H_8$) groups).

Generally, the concentration of the at least one heteroaromatic hydrazone ranges from 0.0005% to 20% by weight, relative to the total weight of the dye composition. For example, the concentration of heteroaromatic hydrazone may range from 0.05% to 10% by weight, relative to the total weight of the dye composition.

The dye composition disclosed herein may optionally contain at least one other oxidation dye precursor. The type of dye precursor (bases and/or couplers) for conventional oxidation used in the composition of the invention is not critical. For example, conventional oxidation bases may be chosen from paraphenylenediamines, bis-phenylalkylenediamines, para-aminophenols, ortho-aminophenols, heterocyclic bases and the addition salts thereof. Among the paraphenylenediamines, the following may be cited as examples: paraphenylenediamine, paratoluylenediamine, 2-chloro paraphenylenediamine, 2,3-dimethyl paraphenylenediamine, 2,6-dimethyl-paraphenylenediamine, 2,6-diethyl paraphenylenediamine, 2,5-dimethyl paraphenylenediamine, N,N-dimethyl para-phenylenediamine, N,N-diethyl paraphenylenediamine, N,N-dipropyl paraphenylenediamine, 4-amino N,N-diethyl 3-methyl aniline, N,N-bis(β-hydroxyethyl) para-phenylenediamine, 4-N,N bis-(13-hydroxyethyl)amino 2-methyl aniline, 4-N,N-bis-(β-hydroxyethyl)amino 2-chloro aniline, 2-β-hydroxyethyl paraphenylene-diamine, 2-fluoro paraphenylenediamine, 2-isopropyl para-phenylenediamine, N-(β-hydroxypropyl) paraphenylene-diamine, 2-hydroxymethyl paraphenylenediamine, N,N-dimethyl 3-methyl paraphenylenediamine, N,N-(ethyl β-hydroxyethyl)paraphenylenediamine, N-(β,γ-dihydroxy-propyl)paraphenylenediamine, N-(4'-aminophenyl) para-phenylenediamine, N-phenyl paraphenylenediamine, 2-β-hydroxyethyloxy paraphenylenediamine, 2-β-acetylaminoethyloxy paraphenylenediamine, N-(β-methoxyethyl) paraphenylenediamine, 4 aminophenyl pyrrolidine, 2 thienyl paraphenylenediamine, 2-β hydroxyethylamino 5-amino toluene, and the addition salts thereof with an acid.

In one embodiment, the at least one other oxidation dye precursor may be a paraphenylenediamine chosen from: paraphenylenediamine, paratoluylenediamine, 2-isopropyl paraphenylenediamine, 2-β-hydroxyethyl paraphenylene-diamine, 2-β-hydroxyethyloxy paraphenylenediamine, 2,6-dimethyl paraphenylenediamine, 2,6-diethyl paraphenylenediamine, 2,3-dimethyl paraphenylenediamine, N,N-bis-(β-hydroxyethyl) paraphenylenediamine, 2-chloro paraphenylenediamine, 2-β-acetylaminoethyloxy para-phenylenediamine, and the acid addition salts thereof.

Among the bis-phenylalkylenediamine, the following may be cited as examples: N,N'-bis-(β-hydroxyethyl) N, N'-bis-(4'-aminophenyl) 1,3-diamino propanol, N,N'-bis-(β-hydroxyethyl) N,N'-bis-(4'-aminophenyl)ethy-lenediamine, N,N'-bis-(4-aminophenyl) tetramethylene-diamine, N,N'-bis-(β-hydroxyethyl) N,N'-bis-(4-amino-phenyl) tetramethylenediamine, N,N'-bis-(4-methyl-aminophenyl)tetramethylenediamine, N,N'-bis-(ethyl) N,N'-bis-(4'-amino 3'methylphenyl)ethylenediamine, 1,8-bis-(2,5-diamino phenoxy)-3,6-dioxaoctane, and the acid addition salts thereof.

Among the para-aminophenols, the following may be: cited as examples: para-aminophenol, 4-amino 3-methyl phenol, 4-amino 3-fluoro phenol, 4-amino 3-hydroxymethyl phenol, 4-amino 2-methyl phenol, 4-amino 2-hydroxymethyl phenol, 4-amino 2-methoxymethyl phenol, 4-amino 2-aminomethyl phenol, 4-amino 2-(β-hydroxyethyl aminomethyl) phenol, 4-amino 2-fluoro phenol, and the acid addition salts thereof.

Among the ortho-aminophenols the following may be cited as examples: 2-amino phenol, 2-amino 5-methyl phenol, 2-amino 6-methyl phenol, 5-acetamido 2-amino phenol and the acid addition salts thereof.

Among the heterocyclic bases, the following may be cited as examples: pyridine derivatives, pyrimidine derivatives and pyrazole derivatives.

The pyridine derivatives, for example, may be chosen from the compounds described in patents GB 1 026 978 and GB 1 153 196, such as 2,5-diamino pyridine, 2-(4-methoxyphenyl) amino3-amino pyridine, 3,4-diamino pyridine, and the acid addition salts thereof.

The pyrimidine derivatives, for example, may be chosen from the compounds described in patents DE 2 359 399; JP 88-169 571; JP 05 163 124; EP 0 770 375 and patent WO 96/15765, such as 2-hydroxy 4,5,6-triaminopyrimidine, 2,4-dihydroxy 5,6-diaminopyrimidine, and pyrazole-pyrimidine derivatives. Examples of the pyrazole-pyrimidine dervatives that may be used are such as those mentioned in patent application FR-A-2 750 048, for example, those chosen from: pyrazolo-[1,5-a]-pyrimidine-3,7-diamine; 2,5-dimethyl pyrazolo-[1,5-a]-pyrimidine-3,7-diamine; pyrazolo[1,5-a]-pyrimidine-3,5-diamine; 2,7-dimethyl pyrazolo-[1,5-a]-pyrimidine-3,5-diamine; 3-amino pyrazolo-[1,5-a]-pyrimidin-7-ol; 3-amino pyrazolo-[1,5-a]-pyrimidin-5-ol; 2-(3-amino pyrazolo-[1,5-a]pyrimidin-7-ylamino)-ethanol, 2-(7-amino pyrazolo-[1,5-a]-pyrimidin-3-ylamino)-ethanol, 2-[(3-amino-pyrazolo[1,5-a]pyrimidin-7-yl)-(2-hydroxy-ethyl)-amino]-ethanol, 2-[(7-amino-pyrazolo [1,5-a]pyrimidin-3-yl)-(2-hydroxy-ethyl)-amino]-ethanol, 5,6-dimethyl pyrazolo-[1,5-a]-pyrimidine-3,7-diamine, 2,6-dimethyl pyrazolo-[1,5-a]-pyrimidine-3,7-diamine, 3-amino-5-methyl-7-imidazolylpropylamino pyrazolo-[1,5-a]-pyrimidine, the acid addition salts thereof, and the tautomer forms thereof when tautomer equilibrium exists.

Examples of pyrazole derivatives that may be used are those chosen from the compounds described in patents DE 3 843 892, DE 4 133 957, and in patent applications WO 94/08969, WO 94/08970, FR-A-2 733 749 and DE 195 43 988, such as those chosen from 4,5-diamino 1-methyl pyrazole, 4,5-diamino 1-(β-hydroxyethyl)pyrazole, 3,4-diamino pyrazole, 4,5-diamino 1-(4'-chlorobenzyl) pyrazole, 4,5-diamino 1,3-dimethyl pyrazole, 4,5-diamino 3-methyl 1-phenyl pyrazole, 4,5-diamino 1-methyl 3-phenyl pyrazole, 4-amino 1,3-dimethyl 5-hydrazino pyrazole, 1-benzyl 4,5-diamino 3-methyl pyrazole, 4,5-diamino 3-tert-butyl 1-methyl pyrazole, 4,5-diamino 1-tert-butyl 3-methyl pyrazole, 4,5 diamino 1-(β-hydroxyethyl) 3-methyl pyrazole, 4,5-diamino 1-ethyl 3-methyl pyrazole, 4,5-diamino 1-ethyl 3-(4'-methoxyphenyl) pyrazole, 4,5-diamino 1-ethyl 3-hydroxymethyl pyrazole, 4,5-diamino 3-hydroxymethyl 1-methyl pyrazole, 4,5-diamino 3-hydroxymethyl 1-isopropyl pyrazole, 4,5-diamino 3-methyl 1-isopropyl pyrazole, 4-amino 5-(2'-aminoethyl)amino 1,3-dimethyl pyrazole, 3,4,5-triamino pyrazole, 1-methyl 3,4,5-triamino pyrazole, 3,5-diamino 1-methyl 4-methylamino pyrazole, 3,5-diamino 4-(β-hydroxyethyl)amino 1-methyl pyrazole, and the acid addition salts thereof.

Generally, the concentration of the optional at least one other oxidation dye precursor ranges from 0.0005% to 10% by weight, relative to the total weight of the composition.

In another embodiment, the optional at least one other oxidation dye precursor may be an oxidation coupler chosen from metaphenylenediamines, metaaminophenols, metadiphenols, naphthalene couplers, heterocylic couplers and the addition salts thereof.

For example, the oxidation coupler may be chosen from: 2-methyl 5-aminophenol, 5-N-(β-hydroxyethyl)amino 2-methyl phenol, 6-chloro-2-methyl-5-aminophenol, 3-amino phenol, 1,3-dihydroxy benzene (or resorcinol), 1,3-dihydroxy 2-methyl benzene, 4-chloro 1,3-dihydroxy benzene, 2,4-diamino 1-(β-hydroxyethyloxy) benzene, 2-amino 4-(β-hydroxy-ethylamino) 1-methoxybenzene, 1,3-diamino benzene, 1,3-bis-(2,4-diaminophenoxy)propane, 3-ureido aniline, 3-ureido 1-dimethylamino benzene, sesamol, 1-β-hydroxyethylamino-3,4-methylenedioxybenzene, β-naphtol, 2 methyl-1-naphtol, 6-hydroxy indole, 4-hydroxy indole, 4-hydroxy N-methyl indole, 2-amino-3-hydroxy pyridine, 6-hydroxy benzomorpholine, 3,5 diamino-2,6-dimethoxypyridine, 1-N-(β-hydroxyethyl)amino-3,4-methy-lene dioxybenzene, 2,6-bis-(β-hydroxyethylamino)toluene, and the addition salts thereof.

Generally, the concentration of the optional at least one other oxidation coupler ranges from 0.0001% to 10% by weight, relative to the total weight of the composition.

As examples, the acid addition salts that may be used for the oxidation bases and couplers can be chosen from hydrochlorates, hydrobromates, sulphates, citrates, succinates, tartrates, lactates, tosylates, benzenesulphonates, phosphates and acetates. In one embodiment, the addition salts which may be used in the dye composition as disclosed herein can be chosen from addition salts with sodium hydroxide, potassium hydroxide, ammonia, amines and alkanolamines.

The dye composition disclosed herein may also optionally contain at least one direct dye. For example, the optional at least one direct dye may be chosen from nitrated dyes in the benzene series, direct cationic dyes, direct azoic, methine, and azomethine dyes.

An appropriate dyeing medium, also called a dye carrier, is generally formed of water or a mixture of water with at least one organic solvent to dissolve those compounds insufficiently soluble in water. Organic solvents that may be used can be chosen from lower $C_1$-$C_4$ alcohols, for example ethanol and isopropanol; polyols and polyol ethers, such as 2-butoxyethanol, propyleneglycol, the monomethylether of propyleneglycol, the monoethylether and monomethylether of diethyleneglycol, and aromatic alcohols, for example, benzyl alcohol and phenoxyethanol, and the mixtures thereof.

The organic solvents may be present in the dye composition in an amount ranging from approximately 1% to 40% by weight, relative to the total weight of the dye composition. For example, the organic solvents may be present in the dye composition in an amount ranging from approximately 5% to 30% by weight, relative to the total weight of the dye composition.

The dye composition disclosed herein may also comprise at least one additive conventionally used in hair dye compositions. For example, such additives may be chosen from anionic, cationic, nonionic, amphoteric, and zwitterionic surfactants; anionic, cationic, nonionic, amphoteric, and zwitterionic polymers; mineral and organic thickening agents (for example, anionic, cationic, nonionic and amphoteric associative polymer thickeners); antioxidant agents, penetration agents, sequestering agents, perfumes, buffers, dispersing agents, conditioning agents (such as volatile and non-volatile silicones that can be either modified or non-modified), film-forming agents, ceramides, preservative agents, and opacifying agents.

The optional at least one additive may be present in the dye composition in an amount ranging from 0.01% and 20% by weight for each additive, relative to the total weight of the dye composition.

Persons of ordinary skill in the art will know how to select these complementary compounds such that the advantageous properties intrinsically attached to the oxidative dye composition disclosed herein are not impaired by the optional addition or additions.

The pH of the dye composition disclosed herein generally ranges from approximately 5 to 11, for example, from 7 to 10. It may be adjusted to the desired value using acidifying or alkalinising agents usually used for dyeing keratin fibers or even using conventional buffer systems.

For example, acidifying agents may be mineral and organic acids chosen from hydrochloric acid, orthophosphoric acid, sulphuric acid, carboxylic acids, such as acetic acid, tartaric acid, citric acid, lactic acid, and sulphonic acids.

The alkalinising agents may be chosen from ammonia, alkaline carbonates, alkanolamines (such as mono-, di-, and triethanolamines and the derivatives thereof), sodium hydroxides, potassium hydroxides, and compounds having the formula (III):

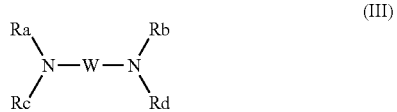

(III)

wherein W is a propylene remainder that may be optionally substituted by a group chosen from hydroxyl and $C_1$-$C_4$ alkyl radicals; Ra, Rb, Rc and Rd, which may be identical or different, are chosen from: hydrogen atoms, $C_1$-$C_4$ alkyl radicals and $C_1$-$C_4$ hydroxyalkyls.

The dye composition may be in various forms, such as liquid, cream, gel form or any other appropriate form to produce a dye for keratin fibers, for example, human hair.

When the at least one aldehyde precursor and at least one enzyme are present within the same dye composition ready for use, said composition is preferably free of gaseous oxygen so as to avoid any early oxidation of the at least one aldehyde precursor.

Still further disclosed herein is a method for dyeing keratin fibers, for example, human keratin fibers such as hair, so that at least one dye composition for dyeing keratin fibers as disclosed herein is applied to keratin fibers, wherein the duration of this application is of sufficient length to develop the desired color. The desired color can be developed by oxygen in air or with the use of an oxidizing agent in relation to the enzyme used. After the dye composition is applied to keratin fibers, it can remain on the keratin fibers for an amount of time ranging from 3 to 60 minutes, for example, from 5 to 40 minutes, after which time the keratin fibers are rinsed, shampooed, rinsed again and dried.

In one embodiment, depending upon the at least one enzyme selected, the dye composition as disclosed herein may be a composition ready for use which, in a medium appropriate for dyeing keratin fibers, comprises at least one aldehyde precursor, at least one enzyme able to generate an aldehyde from the at least one aldehyde precursor and at least one hydrazone, wherein the whole dye composition is stored in anaerobic form, free of gaseous oxygen.

In another embodiment, if the at least one enzyme is able to generate an aldehyde from the at least one aldehyde precursor in the absence of any oxidizing agent or air oxygen, then the components of the presently disclosed dye composition are stored in separate form: a first composition A comprises, in a medium appropriate for dyeing keratin fibers, at least one aldehyde precursor, and a second composition B comprises, in a medium appropriate for dyeing keratin fibers, at least one enzyme able to generate an aldehyde from the at least one aldehyde precursor, wherein at least one of the first composition A and the second composition B also comprises at least one hydrazone. The dyeing method therefore comprises mixing compositions A and B together at the time of use and applying this mixture to the keratin fibers. The method for dyeing keratin fibers, for example, human keratin fibers such as hair, can also be implemented by mixing compositions A and B together on the keratin fibers.

The color can be developed under acid, neutral or alkaline pH.

In one embodiment of the method disclosed herein, the color can be developed using at least one oxidizing agent.

When necessary, at least one oxidizing agent may be added to the dye composition as disclosed herein at the time of use, or it may derive from an oxidizing composition in which it is contained that is applied simultaneously with or sequentially after the dye composition as disclosed herein.

The oxidizing composition may also contain various additives conventionally used in hair dye compositions such as defined above.

The pH of the oxidizing composition containing the at least one oxidizing agent is such that after mixing with the dye composition, the pH of the resulting composition applied to keratin fibers ranges approximately from 5 to 11, for example from 7 to 10. It may be adjusted to the desired value using acidifying or alkalinising agents usually used for dyeing keratin fibers such as defined above.

The dye composition that is applied to keratin fibers may be in various forms, such as liquid, cream or gel form, or in any other form appropriate for dyeing keratin fibers, for example, human hair.

Additionally disclosed herein is a device with several compartments or dye "kit" comprising a first compartment containing a first composition A as defined above, and a second compartment containing a second composition B as defined above. The device or kit may optionally contain a third composition comprising at least one oxidizing agent, wherein the third composition can be contained in a third compartment. In the case that the kit is in the form of a device, the device may be fitted with means enabling the desired mixture to be dispensed on the hair, such as the devices described in patent FR-2 586 913.

The following examples are meant to illustrate the invention without, however, being of a restrictive nature.

EXAMPLES

Example 1

Example 1 demonstrates a reaction conducted in situ for dyeing keratin fibers by enzymatic conversion of ethanol into an acetaldehyde, then coupling the acetaldehyde with N-ethanol pyridine 2-hydrazone.

The reaction was conducted at a pH ranging from 7 to 9 with 30 mM phosphate buffer.

The alcohol oxidase (EC 1.1.3.13) of *Pichia pastoris* was added at a final concentration of 100 U per ml.

The aldehyde precursor used was ethanol, which was added so as to obtain a final in situ concentration of 10% (v/v).

N-ethanol pyridine 2-hydrazone was added to the reaction mixture so as to obtain a final in situ concentration of 0.3M.

The different components were mixed, and applied to keratin fibers that were incubated at 37° C.

The dye composition was allowed to sit on the keratin fibers for 45 minutes, after which, the keratin fibers were washed and rinsed.

The result was keratin fibers with a purple-blue coloring.

Example 2

Example 2 demonstrates a reaction conducted in situ for dyeing keratin fibers by enzymatic conversion of methanol into formaldehyde, then coupling the formaldehyde with 4-methoxy-N-methyl-pyridine-2-hydrazone.

The reaction was conducted at a pH ranging from 7 to 9 with a 30 mM phosphate buffer.

The alcohol oxidase (EC 1.1.3.13) of *Candida boidinii* was added at a final concentration of 100 U per ml.

The aldehyde precursor used was methanol which was added so as to obtain a final in situ concentration of 10% (v/v).

4-methoxy-N-methyl-pyridine-2-hydrazone was added to the reaction mixture so as to obtain a final in situ concentration of 0.3M.

The different components were mixed, and applied to keratin fibers which were then incubated at 37° C.

The dye composition was allowed to sit on the keratin fibers for 45 minutes, after which the keratin fibers were washed and rinsed.

The keratin fibers showed a purple coloring.

Example 3

A—Preparation of *Plectranthus colleoides* (L) Extract

*Plectranthus colleoides* (L) is a plant of the Labiateae family.

The extract used was a raw aqueous extract of *Plectranthus colleoides* (L) taken from the whole plant.

The above-ground part of the plant (leaves and stalks) were sampled, dried at 45° C., crushed in a blade crusher, and the powder obtained was screened through a sifter with a mesh size of 0.5 μm.

The powder was extracted under agitation in the presence of carbonated water pH 9.5 prepared as follows: anhydrous sodium carbonate was added to 1 g/l distilled water, the pH was adjusted to 9.5 by adding 1 N HCl.

The extraction was performed at room temperature to the proportion of 5 g plant powder per 100 ml carbonated water, placed under agitation for 1 h30 at 900 rpm.

The mixture was then vacuum filtered using a filter of 2.7 μm porosity.

The filtrate obtained was then frozen and freeze-dried.

B—Preparation of the Dye Composition

The plant extract was placed in contact with 0.2% of a hydrazone as described above, placed in solution in 100 ml of a (2/5) alcohol/water mixture. The quantity of extract lies ranges from 0.3 to 0.4%. To this mixture 0.5 ml 3% hydrogen peroxide were added with 0.5 ml ammonia buffer pH 9. The composition was placed in contact with keratin fibers and left at room temperature. A purple coloring developed and dyed the keratin fibers.

The same reaction also occurs without the presence of hydrogen peroxide at pH 7.

Colouring results are grouped in the table below.

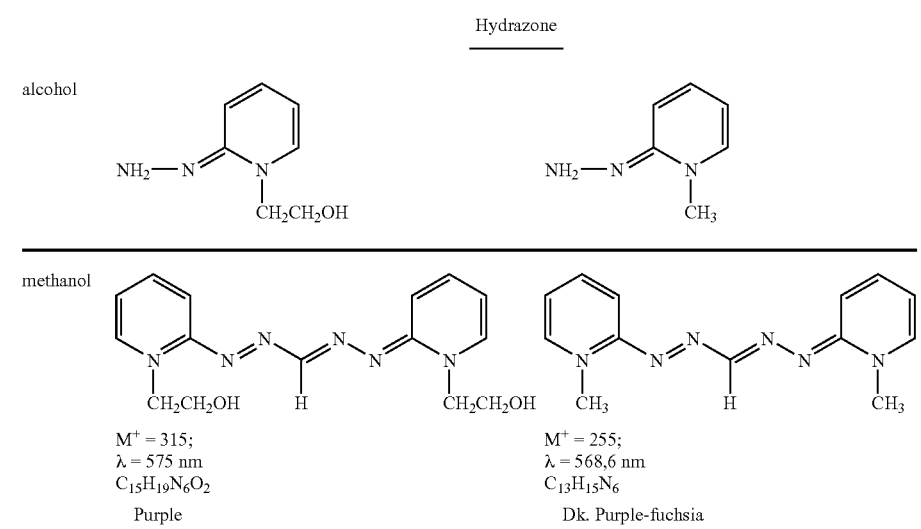

-continued

| | | |
|---|---|---|
| Benzyl alcohol | 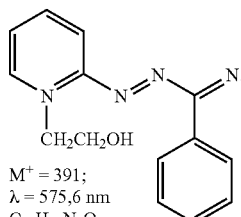<br>$M^+ = 391$;<br>$\lambda = 575{,}6$ nm<br>$C_{21}H_{23}N_6O_2$<br>Purple | 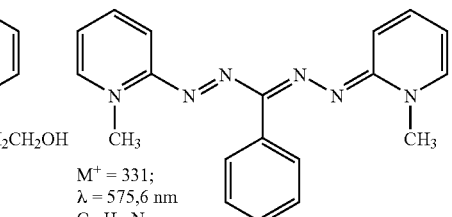<br>$M^+ = 331$;<br>$\lambda = 575{,}6$ nm<br>$C_{19}H_{19}N_6$<br>Purple |
| ethanol | 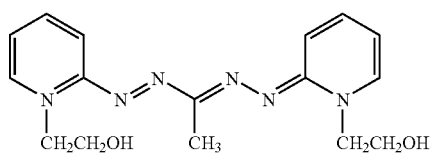<br>$M^+ = 329$;<br>$\lambda = 578{,}6$ nm<br>$C_{16}H_{21}N_6O_2$<br>Purple | 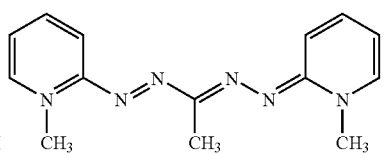<br>$M^+ = 269$;<br>$\lambda = 575{,}6$ nm<br>$C_{14}H_{17}N_6$<br>Dk. Purple-fuchsia |
| alcohol | Hydrazone<br>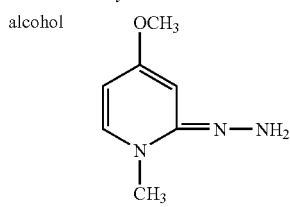 | |
| methanol | 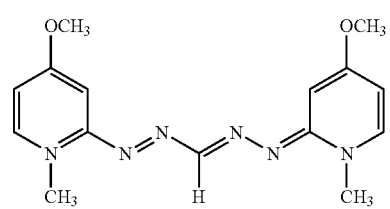<br>$M^+ = 315$;<br>$\lambda = 556$ nm<br>$C_{15}H_{19}N_6O_2$<br>fuchsia | |
| Benzyl alcohol | 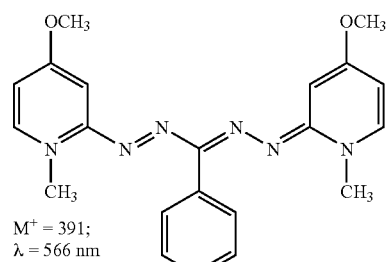<br>$M^+ = 391$;<br>$\lambda = 566$ nm<br>$C_{21}H_{23}N_6O_2$<br>Dark purple | |

-continued

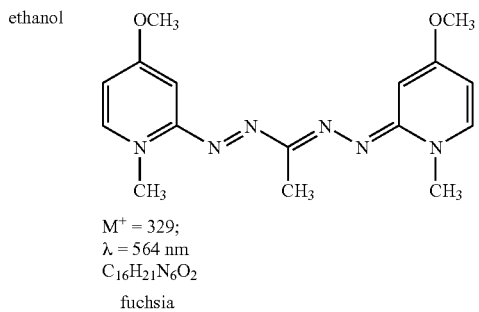

M+ = 329;
λ = 564 nm
C₁₆H₂₁N₆O₂
fuchsia

Dye analysis was performed using HPLC, mass spectroscopy and NMR.

What is claimed is:

1. A dye composition for dyeing keratin fibers comprising, in an appropriate dyeing medium, at least one aldehyde precursor, at least one enzyme able to generate an aldehyde from the at least one aldehyde precursor, and at least one heteroaromatic hydrazone able to generate a colored substance by reaction with an aldehyde;
wherein the at least one heteroaromatic hydrazone is chosen from hydrazones having the formula:

Ar=N—NH₂ wherein Ar is chosen from heterocycles with 5 or 6 links comprising at least one nitrogen atom; and condensed polycyclic heteraromatic groups with 9 or 10 links comprising at least one nitrogen atom, and
wherein Ar can optionally be substituted on the nitrogen atoms by a substituent chosen from $C_1$ to $C_4$ alkyls, $C_1$ to $C_4$ alcohols, and $C_1$ to $C_4$ ethers.

2. The dye composition according to claim 1, wherein the at least one enzyme is derived from an extract chosen from plant, animal, microorganism, virus, differentiated cell and dedifferentiated cell extracts, and wherein said at least one enzyme may or may not be obtained in vivo or in vitro, may or may not be genetically modified, and may or may not be obtained by chemical or biotechnological synthesis.

3. The dye composition according to claim 2, wherein the at least one enzyme is derived from a species chosen from *Plectranthus, Pinus, Gastropoda, Manduca, Pichia, Candida, Pleurotus,* and *Pseudomonas.*

4. The dye composition according to claim 3, wherein the at least one enzyme is derived from a species chosen from: *Plectranthus colleoides, Pinus strobus, Gastropoda mollusc, Manduca sexta, Pichia pastoris, Candida boidinii, Pleurotus pulmonarius* and *Pseudomonas pseudoalcaligenes.*

5. The dye composition according to claim 1, wherein the at least one enzyme is present in the dye composition in a concentration ranging from 0.005% to 40% by weight, relative to the total weight of said dye composition.

6. The dye composition according to claim 1, wherein the at least one aldehyde precursor is an alcohol chosen from amino acids, 2-oxo acids, and primary alcohols.

7. The dye composition according to claim 6, wherein the alcohols from amino acids are chosen from N-6 methyl lysine, dimethylglycine, methyl glutamate, threonine and sarcosine.

8. The dye composition according to claim 6, wherein the 2-oxo acids are chosen from: 2-oxoacidpyruvate, benzoylformate, and phenyl pyruvate.

9. The dye composition according to claim 6, wherein the primary alcohols are chosen from methanol, ethanol, and benzyl alcohol.

10. The dye composition according to claim 6, wherein the concentration of the at least one aldehyde precursor ranges from 0.01% to 40% by weight, relative to the total weight of the composition.

11. The dye composition according to claim 1, wherein the concentration of the at least one heteroaromatic hydrazone ranges from 0.0005% to 20% by weight, relative to the total weight of the composition.

12. The dye composition according to any of claim 1, further comprising at least one oxidation base chosen from paraphenyldiamines, bis-phenylalkylenediamines, para-aminophenols, ortho-aminophenols, heterocyclic bases, and the addition salts thereof.

13. The dye composition according to claim 12, wherein the concentration of the at least one oxidation base in the dye composition ranges from 0.0005% to 10% by weight, relative to the total weight of the dye composition.

14. The dye composition according to claim 1, further comprising at least one oxidation coupler chosen from metaphenylenediamines, metaaminophenols, metadiphenols, naphthalene couplers, heterocyclic couplers, and the addition salts thereof.

15. The dye composition according to claim 14, wherein the concentration of the at least one coupler in the dye composition ranges from 0.0001% to 10% by weight relative to the total weight of the composition.

16. The dye composition according to claim 1, further comprising at least one direct dye.

17. The dye composition according to claim 1, further comprising at least one oxidizing agent.

18. A method for dyeing keratin fibers, comprising:
applying to said keratin fibers a dye composition comprising, in an appropriate dyeing medium, at least one aldehyde precursor, at least one enzyme able to generate an aldehyde from the at least one aldehyde precursor, and at least one heteroaromatic hydrazone, able to generate a colored substance by reaction with an aldehyde, and
leaving said dyeing composition on said keratin fibers for a time sufficient to develop a desired color on the keratin fibers;
wherein the at least one heteroaromatic hydrazone is chosen from hydrazones having the formula:

Ar=N—NH₂ wherein Ar is chosen from heterocycles with 5 or 6 links comprising at least one nitrogen atom; and condensed polycyclic heteroaromatic groups with 9 or 10 links comprising at least one nitrogen atom, and
wherein Ar can optionally be substituted on the nitrogen atoms having by a substituent chosen from $C_1$ to $C_4$ alkyls, $C_1$ to $C_4$ alcohols, and $C_1$ to $C_4$ ethers.

19. The method according to claim 18, wherein the keratin fibers are human keratin fibers.

20. The method according to claim 19, wherein the human keratin fibers are hair.

21. The method according to claim 18, wherein said time sufficient ranges from approximately 3 to 60 minutes.

22. The method according to claim 21, wherein said time sufficient ranges from approximately 5 to 40 minutes.

23. The method according to claim 18, further comprising, after the color is developed, rinsing said keratin fibers, shampooing said keratin fibers, rinsing again, and drying said keratin fibers.

24. The method according to claim 18, wherein the dye composition applied to said keratin fibers further comprises at least one oxidation base chosen from paraphenyldiamines, bis-phenylalkylenediamines, para-aminophenols, ortho-aminophenols, heterocyclic bases, and the addition salts thereof.

25. The method according to claim 18, wherein the dye composition applied to said keratin fibers further comprises at least one oxidation coupler chosen from metaphenylenediamines, metaaminophenols, metadiphenols, naphthalene couplers, heterocyclic couplers, and the addition salts thereof.

26. The method according to claim 18, wherein the dye composition applied to said keratin fibers further comprises at least one direct dye.

27. The method according to claim 18, wherein said color is developed using an oxidizing agent.

28. The method according to claim 27, wherein said oxidizing agent is added to the dye composition at the time of use or is comprised in an oxidizing composition which may be applied to the keratin fibers simultaneously with or sequentially after the dye composition.

29. The method according to claim 18, wherein the dye composition applied to said keratin fibers is a ready-to-use composition stored in anaerobic form free of gaseous oxygen.

30. The method according to claim 18, wherein said at least one aldehyde precursor, said at least one enzyme able to generate an aldehyde from the at least one aldehyde precursor, and said at least one heteroaromatic hydrazone, are mixed together, in the appropriate dyeing medium, on the keratin fibers.

31. A method for dyeing keratin fibers, comprising
mixing a first composition with a second composition to form a ready-to-use dye composition, wherein
said first composition comprises, in an appropriate dyeing medium, at least one aldehyde precursor, and
said second composition comprises, in an appropriate dyeing medium, at least one enzyme able to generate an aldehyde from the at least one aldehyde precursor,
and further wherein at least one of said first composition and said second composition additionally comprises at least one heteroaromatic hydrazone able to generate a colored substance by reaction with an aldehyde, and
applying said ready-to-use dye composition to the keratin fibers;
wherein the at least one heteroaromatic hydrazone is chosen from hydrazones having the formula:

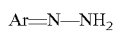

$$Ar=N-NH_2$$

wherein Ar is chosen from heterocycles with 5 or 6 links comprising at least one nitrogen atom; and condensed polycyclic heteroaromatic groups with 9 or 10 links comprising at least one nitrogen atom, and
wherein Ar can optionally be substituted on the nitrogen atoms by a substituent chosen from $C_1$ to $C_4$ alkyls, $C_1$ to $C_4$ alcohols, and $C_1$ to $C_4$ ethers.

32. The method according to claim 31, wherein the color is developed using an oxidizing agent.

33. The method according to claim 31, wherein said first composition and said second composition are mixed together on the keratin fibers.

34. The method according to claim 32, wherein said oxidizing agent is added to the ready-to-use dye composition at the time of use or is comprised in an oxidizing composition which may be applied to the keratin fibers simultaneously with or sequentially after the ready-to-use dyeing composition.

35. A multi-compartment device for dyeing keratin fibers comprising a first compartment comprising a first composition, and a second compartment comprising a second composition, wherein
said first composition comprises, in an appropriate dyeing medium, at least one aldehyde precursor;
said second composition comprises, in an appropriate dyeing medium, at least one enzyme able to generate an aldehyde from the at least one aldehyde precursor; and
wherein at least one of said first composition and said second composition further comprises at least one heteroaromatic hydrazone able to generate a colored substance by reaction with an aldehyde;
wherein the at least one heteroaromatic hydrazone is chosen from hydrazones having the formula:

$$Ar=N-NH_2$$

wherein Ar is chosen from heterocycles with 5 or 6 links comprising at least one nitrogen atom; and condensed polycyclic heteroaromatic groups with 9 or 10 links comprising at least one nitrogen atom, and
wherein Ar can optionally be substituted on the nitrogen atoms by a substituent chosen from $C_1$ to $C_4$ alkyls, C1 to C4 alcohols, and $C_1$ to $C_4$ ethers.

* * * * *